(12) United States Patent
Salciccioli et al.

(10) Patent No.: US 10,351,489 B2
(45) Date of Patent: Jul. 16, 2019

(54) PROCESSES FOR RECOVERING PARAXYLENE

(71) Applicant: ExxonMobil Chemical Patents Inc., Baytown, TX (US)

(72) Inventors: Michael Salciccioli, Houston, TX (US); Gaurav Agrawal, Raritan, NJ (US); Michael W. Weber, Houston, TX (US); Dana L. Pilliod, League City, TX (US); Catherine M. Dorsi, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/600,494

(22) Filed: May 19, 2017

(65) Prior Publication Data

US 2018/0002252 A1 Jan. 4, 2018

Related U.S. Application Data

(60) Provisional application No. 62/356,634, filed on Jun. 30, 2016.

(30) Foreign Application Priority Data

Aug. 25, 2016 (EP) .................................... 16185649

(51) Int. Cl.
C07C 5/13 (2006.01)
C07C 7/12 (2006.01)
(Continued)

(52) U.S. Cl.
CPC ................ C07C 5/13 (2013.01); C07B 63/04 (2013.01); C07C 5/277 (2013.01); C07C 5/2708 (2013.01);
(Continued)

(58) Field of Classification Search
CPC .. C07C 5/13; C07C 15/08; C07C 7/13; C07C 7/12; C07C 2601/16
See application file for complete search history.

(56) References Cited

U.S. PATENT DOCUMENTS 3,201,491 A 8/1965 Stine et al.
3,354,078 A 11/1967 Miale et al.
(Continued)

FOREIGN PATENT DOCUMENTS

WO 2016/008654 A1 1/2016

OTHER PUBLICATIONS

Weisz, P. B., et al., "Superactive Crystalline Aluminosilicate Hydrocarbon Catalysts", Journal Of Catalysis, vol. 4, Issue 4, pp. 527-529, Aug. 1965.
(Continued)

Primary Examiner — Youngsul Jeong

(57) ABSTRACT

Disclosed is a process for recovering paraxylene in which a first simulated moving bed adsorption unit is used to produce two extract streams—one rich in paraxylene and a paraxylene-rich extract stream that is lean in ethylbenzene and an ethylbenzene-rich extract stream that is lean in paraxylene- and a paraxylene-depleted raffinate stream. A significant amount of the ethylbenzene is removed in the ethylbenzene-rich extract stream (at least enough to limit buildup in the isomerization loop), so the paraxylene-depleted raffinate stream may be isomerized in the liquid phase. Avoiding vapor phase isomerization saves energy and capital, as liquid phase isomerization requires less energy and capital than the vapor phase isomerization process due to the requirement of vaporizing the paraxylene-depleted stream and the use of hydrogen, which requires an energy and capital intensive hydrogen recycle loop.

22 Claims, 8 Drawing Sheets

(51) Int. Cl.
*C07C 15/08* (2006.01)
*C07C 7/13* (2006.01)
*C07C 7/11* (2006.01)
*C07B 63/04* (2006.01)
*C07C 5/27* (2006.01)
*C07C 7/148* (2006.01)

(52) U.S. Cl.
CPC .................. *C07C 7/11* (2013.01); *C07C 7/12* (2013.01); *C07C 7/13* (2013.01); *C07C 7/148* (2013.01); *C07C 15/08* (2013.01); *C07C 2601/16* (2017.05)

(56) References Cited

U.S. PATENT DOCUMENTS

| | | | |
|---|---|---|---|
| 3,702,886 A | 11/1972 | Argauer et al. | |
| 3,709,979 A | 1/1973 | Chu | |
| 3,832,449 A | 8/1974 | Rosinski et al. | |
| 4,016,218 A | 4/1977 | Haag et al. | |
| 4,016,245 A | 4/1977 | Plank et al. | |
| 4,076,842 A | 2/1978 | Plank et al. | |
| 4,117,026 A | 9/1978 | Haag et al. | |
| RE29,948 E | 3/1979 | Dwyer et al. | |
| 4,159,282 A | 6/1979 | Olson et al. | |
| 4,397,827 A | 8/1983 | Chu | |
| 4,439,409 A | 3/1984 | Puppe et al. | |
| RE31,782 E | 12/1984 | Olson et al. | |
| 4,556,477 A | 12/1985 | Dwyer | |
| 4,582,815 A | 4/1986 | Bowes | |
| 4,826,667 A | 5/1989 | Zones et al. | |
| 4,954,325 A | 9/1990 | Rubin et al. | |
| 5,053,374 A | 10/1991 | Absil et al. | |
| 5,173,461 A | 12/1992 | Absil et al. | |
| 5,182,242 A | 1/1993 | Marler | |
| 5,236,575 A | 8/1993 | Bennett et al. | |
| 5,250,277 A | 10/1993 | Kresge et al. | |
| 5,362,697 A | 11/1994 | Fung et al. | |
| 5,948,950 A * | 9/1999 | Hotier et al. | C07C 7/13 585/828 |
| 6,004,452 A | 12/1999 | Ash et al. | |
| 6,369,287 B1 | 4/2002 | Magne-Drisch et al. | |
| 6,376,734 B1 | 4/2002 | Magne-Drisch et al. | |
| 6,423,879 B1 | 7/2002 | Brown et al. | |
| 6,504,072 B1 | 1/2003 | Brown et al. | |
| 7,893,309 B2 | 2/2011 | Guillon et al. | |
| 7,915,471 B2 | 3/2011 | Leflaive et al. | |
| 8,293,963 B2 * | 10/2012 | Zhong et al. | C07C 7/14 585/812 |
| 8,569,559 B2 | 10/2013 | Ou | |
| 2008/0262282 A1 * | 10/2008 | Leflaive et al. | C07C 15/08 585/745 |
| 2015/0266794 A1 | 9/2015 | Ou et al. | |

OTHER PUBLICATIONS

Miale, J. N., et al., "Catalysis by Crystalline Aluminosilicates, IV. Attainable Catalytic Cracking Rate Constants, and Superactivity" Journal of Catalysis, vol. 6, Issue 2, pp. 278-287, Oct. 1966.
Olson, D. H., et al., "Chemical and Physical Properties of the ZSM-5 Substitutional Series", Journal of Catalysis, vol. 61, Issue 2, pp. 390-396, Feb. 1980.
Minceva, M., et al., "Modeling and Simulation of a Simulated Moving Bed for the Separation of P-Xylene", Industrial & Engineering Chemistry Research, vol. 41, pp. 3454-3461, 2002.
Kurup, A.S., et al., "Comparative Study of Modified Simulated Moving Bed Systems at Optimal Conditions for the Separation of Ternary Mixtures of Xylene Isomers", Ind. Eng. Chem. Res., vol. 45, Issue 18, pp. 6251-6265, Aug. 2006, DOI: 10.1021/ie0505413.
U.S. Appl. No. 15/600,494, filed May 19, 2017.

\* cited by examiner

PROCESSES FOR RECOVERING PARAXYLENE

PRIORITY CLAIM

This application claims priority to U.S. Provisional Application Ser. No. 62/356,634 filed Jun. 30, 2016 and European Application No. 16185649.7 filed Aug. 25, 2016, the disclosures of which are fully incorporated herein by their reference.

TECHNICAL FIELD

This application relates to an improved process for producing paraxylene, particularly the recovery of paraxylene from streams containing ethylbenzene.

BACKGROUND

Ethylbenzene (EB), paraxylene (PX), orthoxylene (OX), and metaxylene (MX) are often present together in $C_8$ aromatic product streams from chemical plants and oil refineries. High purity EB is an important raw material for the production of styrene; however, for a variety of reasons all high purity EB feedstocks used in styrene production are produced by alkylation of benzene with ethylene, rather than by recovery from a $C_8$ aromatics stream. Of the three xylene isomers, PX has the largest commercial market and is used primarily for manufacturing terephthalic acid and terephthalate esters for use in the production of various polymers such as poly(ethylene terephthalate), poly(propylene terephthalate), and poly(butene terephthalate). While OX and MX are useful as solvents and raw materials for making products such as phthalic anhydride and isophthalic acid, market demand for OX and MX and their downstream derivatives is much smaller than that for PX.

Given the higher demand for PX as compared with its other isomers, there is significant commercial interest in maximizing PX production from any given source of $C_8$ aromatic materials. However, there are a number of major technical challenges to be overcome in achieving this goal of maximizing PX yield. For example, the four $C_8$ aromatic compounds, particularly the three xylene isomers, are usually present in concentrations dictated by the thermodynamics of production of the $C_8$ aromatic stream in a particular plant or refinery. As a result, the PX production is limited, at most, to the amount originally present in the $C_8$ aromatic stream unless additional processing steps are used to increase the amount of PX and/or to improve the PX recovery efficiency. A variety of methods are known to increase the concentration of PX in a $C_8$ aromatics stream. These methods normally involve cycling the stream between a separation step, in which at least part of the PX is recovered to produce a PX-depleted stream, and a xylene isomerization step, in which the PX content of the PX-depleted stream is returned back towards equilibrium concentration.

In a typical aromatics plant, such as that shown in FIG. 1, liquid feed, typically a $C_{8+}$ aromatic feedstream which has previously been processed by known methods to remove $C_{7-}$ species (particularly benzene and toluene), is fed by conduit 1 to xylenes re-run 3, an apparatus per se well known in the art. The xylenes re-run (or more simply a fractionation column) 3 vaporizes the feed and separates the $C_8$ aromatics into an overhead mixture 5 of xylenes and EB, and a bottom product 61 comprising $C_{9+}$ aromatics. The overhead mixture typically has a composition of about 40-50% MX, 15-25% PX, 15-25% OX, and 10-20% EB. Unless otherwise noted herein, percentages are % weight. The overhead is then condensed in condenser 7, an apparatus also per se well-known in the art, and becomes the feed for the PX recovery unit 15, via conduit 9 and 13, a portion of the condensed overhead may be returned to re-run 3 as reflux via conduits 9 and 11.

The PX recovery unit 15 may employ crystallization technology, adsorption technology, or membrane separation technology, each per se well known in the art. These technologies separate PX from its isomers and are capable of producing high purity PX up to 99.9%, which is taken from unit 15 via conduit 17. Shown in FIG. 1 is the case where unit 15 is an adsorptive separation unit, such as a Parex™ or Eluxyl™ unit, in which case typically the extract 17, which comprises a desorbent, such as paradiethylbenzene (PDEB), needs to be separated, such as by distillation, from the desired extract PX in distillation column 19, which generates an overhead 23 that is condensed in condenser 25 to yield a liquid stream 27, which is a high purity PX stream. This stream 27 may be taken off via conduit 31 and optionally a portion may be returned to column 19 as reflux via conduit 29. The desorbent is returned to the PX recovery system 15 via conduit 21. Raffinate from the recovery system 15, comprising MX, OX, EB, and some PX, is removed via conduit 65 and sent to unit 37, discussed below. Note: a portion of raffinate in 65 may be recovered and marketed as low-value solvent xylene.

The raffinate 65, which comprises mainly MX, OX, EB, and desorbent is sent to fractionation column 37, generating overhead 33 and bottoms 63. Overhead 33 contains MX, OX and EB, which is condensed in condenser 32 and sent via conduit 35 and then 41 to isomerization unit 43, discussed in more detail below. A portion may be returned to fractionator 37 via conduit 35 and then 39 as reflux. The desorbent in the bottoms product is returned to 15. Note that as used herein the term "raffinate" is used to mean the portion recovered from the PX recovery unit 15, whether the technology used is adsorptive separation, crystallization, or membrane, and then is sent to the isomerization unit 43, conventionally a vapor phase isomerization unit, which uses technology also per se well-known.

A stream consisting essentially of MX, OX, and EB is sent to isomerization unit 43, an apparatus per se known in the art, to isomerize the MX and OX and optionally EB to PX. Isomerization unit 43 may be a vapor phase or liquid phase isomerization unit. Conventionally there are one or more heat exchangers or furnaces associated with the system shown in FIG. 1 between the PX recovery unit 15 and the isomerization unit that are not shown for convenience of view. Likewise, hydrogen separators and hydrogen compressors are also not shown for convenience of view. These and other features, such as valves and the like, would be apparent to one of ordinary skill in the art.

The product of the isomerization unit 43 is sent via conduit 51 to the $C_{7-}$ distillation tower 53, which separates the product of isomerization into a bottom stream 59 comprising equilibrium xylenes and the overhead 47, comprising $C_{7-}$ aromatics, e.g., benzene and toluene. The overhead product is condensed in condenser 45 and then the distribution of liquid product via conduit 49 may be apportioned as desired between conduit 57 and conduit 55, the former of which may be disposed of in numerous ways which would be well-known per se in the art, and the latter conduit returning $C_{7-}$ aromatics as reflux to tower 53. The bottoms product 59 of distillation tower 53 is then sent to xylenes re-run 3, either merging with feed 1 as shown in the figure, or it may be introduced by a separate inlet (not shown).

Vapor phase isomerization of the raffinate's EB is generally needed to limit EB buildup in the recycle stream 59. However, vapor phase isomerization has many disadvantages, including high energy consumption, costly and complex process equipment, and high xylenes loss due to conversion of the xylenes in the raffinate into undesirable products such as light gases and heavy aromatics, e.g., by one or more side-reactions such as one or more of cracking, transalkylation, or disproportionation. Attempts to overcome these disadvantages include reducing the quantity of raffinate going to the vapor phase isomerization, e.g., removing EB from the raffinate by using chromatographic EB separation in the PX recovery unit, as disclosed in U.S. Pat. No. 7,915,471 and U.S Patent Publication No. 2015/0266794. The separated EB is isomerized in a vapor phase isomerization stage, with the remainder of the raffinate being isomerized in a liquid phase isomerization stage. The liquid phase isomerization stage is operated under conditions which lessen undesired cracking, transalkylation, and disproportionation side-reactions. Isomerates from the vapor phase and liquid phase isomerization stages are then combined and recycled to the xylene re-run column.

Even when EB is separated for vapor phase isomerization, with the remainder of the PX-depleted raffinate subjected to liquid phase isomerization, the vapor phase isomerization stage contributes to xylene loop inefficiencies. Some of these inefficiencies result from one or more of (i) the need to vaporize the separated EB and then re-condense the vapor phase isomerate for combining with the isomerate derived from the liquid phase isomerization stage, (ii) the need to separate unreacted molecular hydrogen vapor for re-use as an isomerization treat gas, and (iii) the need for removing non-aromatics formed during isomerization. Consequently, it is desired to further lessen or even eliminate the need for vapor phase isomerization.

BRIEF SUMMARY

Embodiments disclosed herein are directed to processes for recovering PX in which a first simulated moving bed adsorption unit is used to produce two extract streams—a PX-rich extract stream that is lean in EB, and an EB-rich extract stream that is lean in PX—and a PX-depleted raffinate stream. A significant amount of the EB is removed in the EB-rich extract stream (at least enough to limit buildup in the isomerization loop), so the PX-depleted raffinate stream may be isomerized in the liquid phase. Avoiding vapor phase isomerization saves energy and capital, as liquid phase isomerization requires less energy and capital than the vapor phase isomerization process due to the requirement of vaporizing the PX-depleted stream and the use of hydrogen, which requires an energy- and capital-intensive hydrogen recycle loop. Liquid phase isomerization also reduces the destruction of xylene molecules into less valuable non-aromatics. PX and EB may be recovered from the EB-rich extract stream, or PX may be recovered and the remaining $C_8$ isomers may be isomerized in the vapor phase to produce more PX.

In some embodiments, the process comprises introducing a first hydrocarbon feed stream, which comprises a mixture of PX, MX, OX, and EB, and a desorbent stream, which comprises desorbent, into a first simulated moving bed adsorption unit. A first PX-rich extract stream, which comprises desorbent and PX, is withdrawn from the first simulated moving bed adsorption unit at a location downstream of the desorbent introduction location and upstream of the feed introduction location. In addition an EB-rich extract stream, which comprises desorbent, EB, and PX, is withdrawn from the first simulated moving bed adsorption unit at a location downstream of the PX-rich extract stream withdrawal location and upstream of the feed introduction location. Further, a first PX-depleted raffinate stream, which comprises desorbent, MX, OX, and EB, is also withdrawn from the first simulated moving bed adsorption unit.

At least a portion of the first PX-depleted raffinate stream is isomerized in the liquid phase to produce a first isomerized stream having a higher PX concentration than the first PX-depleted raffinate stream, and the first isomerized stream is recycled to the first simulated moving bed adsorption unit. The EB-rich extract stream may be sent to a PX recovery unit to produce a second PX-rich extract stream and either recover a pure EB stream or isomerize the remaining $C_8$ isomers isomerized in the vapor phase to produce more PX. In one embodiment, the PX recovery unit is a second simulated moving bed adsorption unit. In another embodiment, the second PX recovery unit is a crystallizer.

These and other objects, features, and advantages of the disclosed embodiments will become apparent in the following detailed description, drawings, specific embodiments, experiments, and accompanying claims.

DETAILED DESCRIPTION

As used herein the term "$C_n$" hydrocarbon, wherein n is a positive integer, means a hydrocarbon having n number of carbon atom(s) per molecule. For example, a $C_8$ aromatic hydrocarbon means an aromatic hydrocarbon or mixture of aromatic hydrocarbons having 8 carbon atom(s) per molecule. The term "$C_n+$" hydrocarbon, wherein n is a positive integer, means a hydrocarbon having at least n number of carbon atom(s) per molecule, whereas the term "$C_n-$" hydrocarbon wherein n is a positive integer, means a hydrocarbon having no more than n number of carbon atom(s) per molecule.

Figure 2:
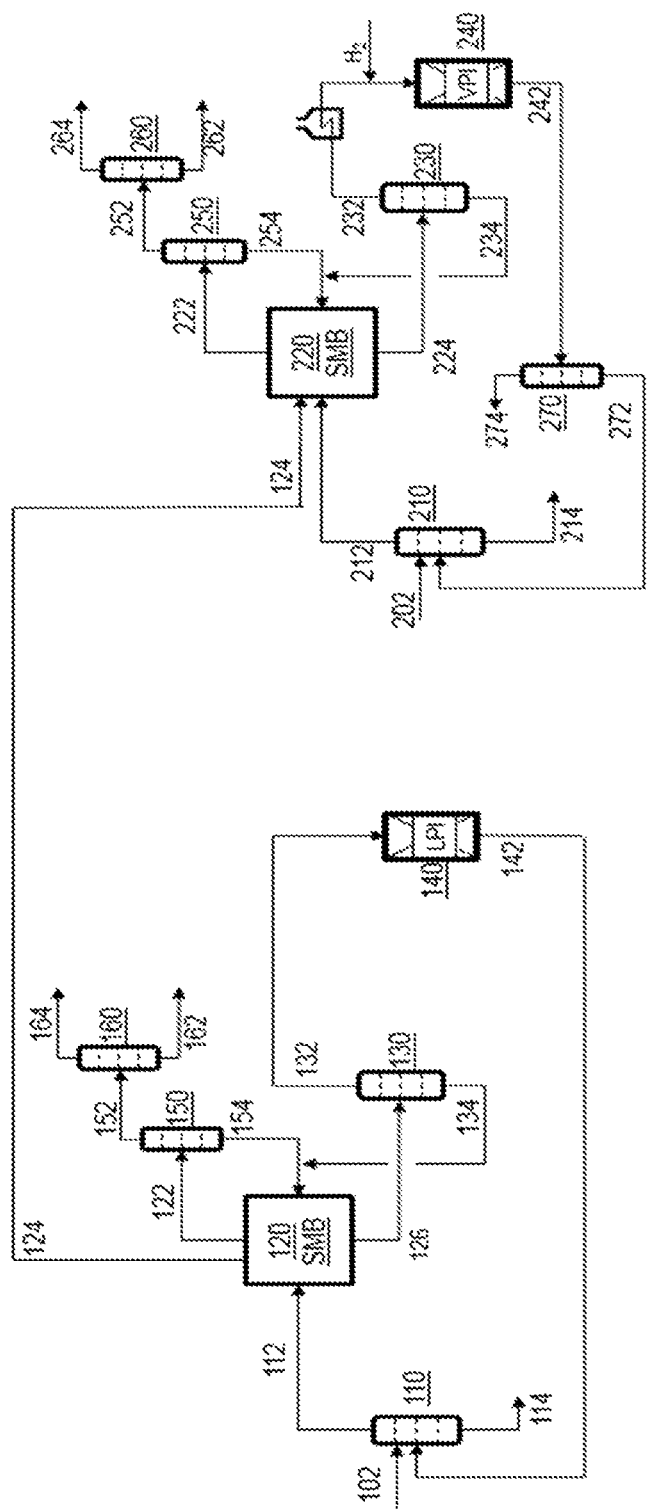
FIG. 2 illustrates a PX production and extraction process in accordance with at least some embodiments disclosed herein.
Figure 3:
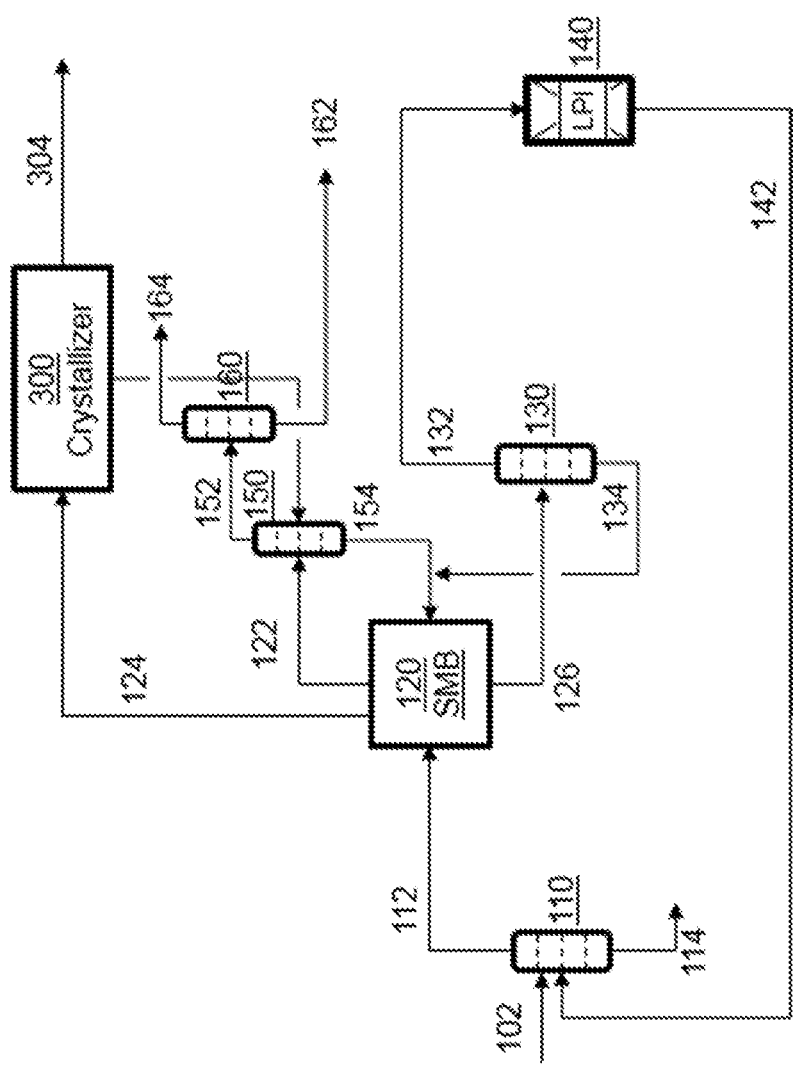
FIG. 3 illustrates another PX production and extraction process in accordance with at least some embodiments disclosed herein.

Embodiments disclosed herein include improved processes for recovering PX. With reference to FIGS. 2 and 3, a first hydrocarbon feed 102 comprising xylenes and EB is provided to a first simulated moving bed adsorption unit 120, where a PX-rich extract stream 122, an EB-rich extract stream 124, and a PX-depleted raffinate stream 126 are recovered. The PX-depleted raffinate stream 126 is passed to a xylene isomerization unit 140 where the PX-depleted raffinate stream 126 is isomerized under at least partial liquid phase conditions to produce an isomerized stream 142 having a higher PX concentration than the PX-depleted raffinate stream 126. The isomerized stream 142 is then recycled to the first PX recovery unit 120 to recover additional PX and the process is repeated.

Figure 1:
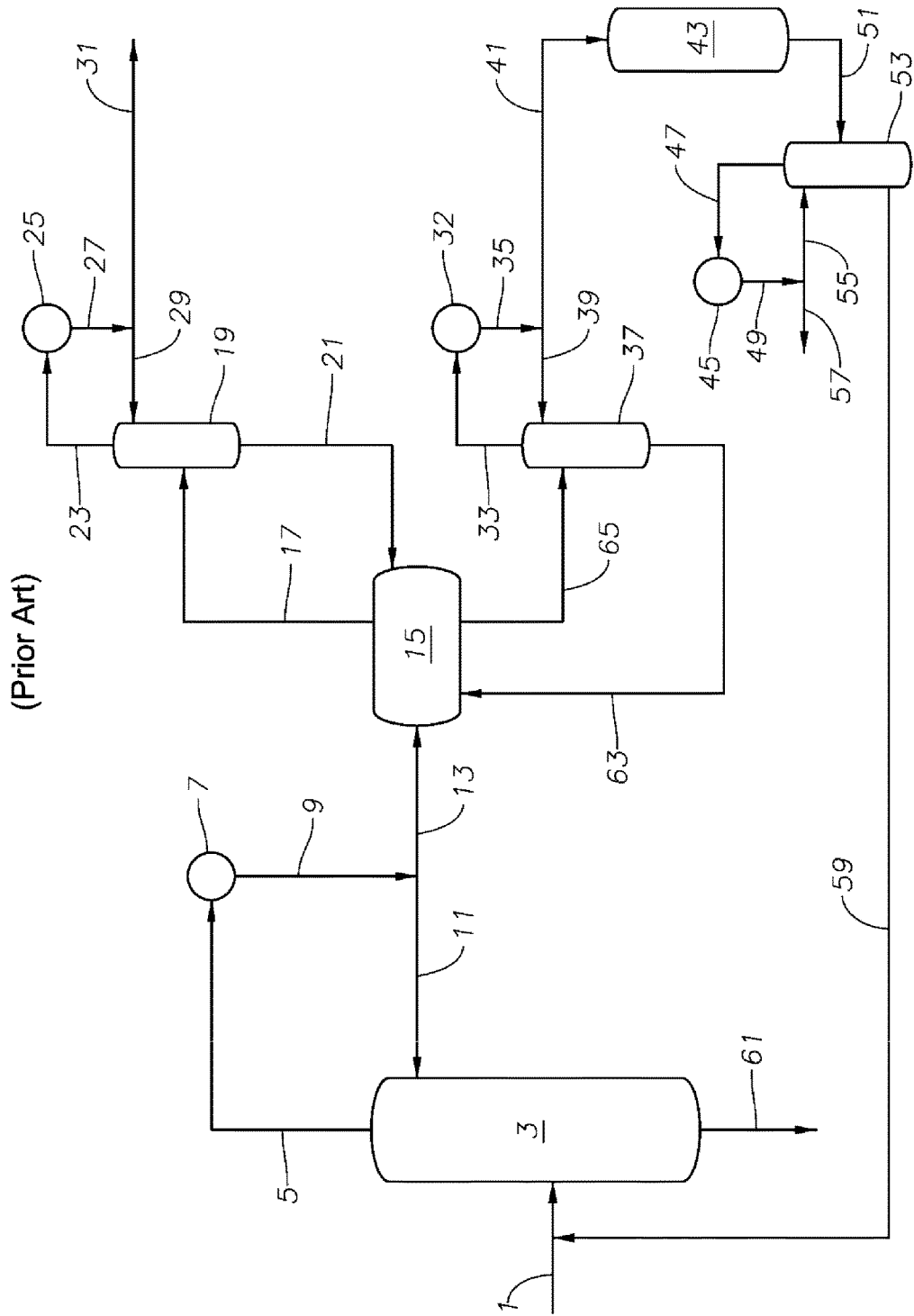
FIG. 1 illustrates a conventional PX production and extraction process.

Optionally, the EB-rich extract stream 124 is further processed in a PX recovery unit to recover additional PX. In one embodiment (e.g., see FIG. 1), the PX recovery unit is a second simulated moving bed adsorption unit 220. When the second simulated moving bed adsorption unit 220 is used, the EB-rich extract stream 124 may or may not pass through a fractionation tower to remove the desorbent before the second simulated moving bed adsorption unit 220. The EB-rich extract stream 124 may also be combined with a second hydrocarbon feed 202 prior to the second simulated moving bed adsorption unit 220. In another embodiment (e.g., see FIG. 2), the PX recovery unit is a crystallizer 300 and the EB-rich extract stream 124 may or may not pass through a fractionation tower to remove the desorbent before the crystallizer 300. In yet another embodiment, the EB-rich extract stream 124 is sent to the refinery for further processing or for the motor gasoline pool.

The first hydrocarbon feed stream 102 employed in the present process may be any hydrocarbon stream containing $C_8$ aromatic hydrocarbons, such as a reformate stream (product stream of a reformate splitting tower), a hydrocracking product stream, a xylene or EB reaction product stream, an aromatic alkylation product stream, an aromatic disproportionation stream, an aromatic transalkylation stream, a methanol to aromatic product stream, and/or a Cyclar™ process stream.

In one embodiment, the feed is the product of the alkylation of benzene and/or toluene with methanol and/or dimethyl ether in a methylation reactor. One such methylation reactor is described in U.S. Pat. Nos. 6,423,879 and 6,504,072, the entire contents of which are incorporated herein by reference, and employs a catalyst comprising a porous crystalline material having a Diffusion Parameter for 2,2 dimethylbutane of about 0.1-15 $sec^{-1}$ when measured at a temperature of 120° C. and a 2,2 dimethylbutane pressure of 60 torr (8 kPa). The porous crystalline material may be a medium-pore zeolite, such as ZSM-5, which has been severely steamed at a temperature of at least 950° C. in the presence of at least one oxide modifier, for example, including phosphorus, to control reduction of the micropore volume of the material during the steaming step. Such a methylation reactor is hereinafter termed a "PX-selective methylation reactor".

The feed to the PX recovery section may further comprise recycle stream(s) from the isomerization step(s) and/or various separating steps. The hydrocarbon feed comprises PX, together with MX, OX, and EB. In addition to xylenes and EB, the hydrocarbon feedstock may also contain certain amounts of other aromatic or even non-aromatic compounds. Examples of such aromatic compounds are $C_{7-}$ hydrocarbons, such as benzene and toluene, and $C_{9+}$ aromatics, such as mesitylene, pseudo-cumene and others. These types of feedstream(s) are described in "Handbook of Petroleum Refining Processes", Eds. Robert A. Meyers, McGraw-Hill Book Company, Second Edition.

The first hydrocarbon feed 102 is initially supplied to a first simulated moving bed adsorption unit 120 to recover a first PX-rich extract stream 122, an EB-rich extract stream 124, and a PX-depleted raffinate stream 126. Depending on the composition of the hydrocarbon feed 102, one or more initial separation steps that serve to remove $C_{7-}$ and $C_{9+}$ hydrocarbons from the feed may occur. Generally the initial separation steps may include fractional distillation, crystallization, adsorption, a reactive separation, a membrane separation, extraction, or any combination thereof. In embodiments, shown in FIGS. 2 and 3, before going to the first simulated moving bed unit 120, the first hydrocarbon feed 102 is passed through a xylenes fractionation tower 110 prior to passing to the PX recovery unit 120. The xylenes fractionation tower 110 produces an overhead stream 112 comprising $C_8$ hydrocarbons and a bottoms stream 114 containing $C_{9+}$ hydrocarbons. The overhead stream 112 comprising $C_8$ hydrocarbons is sent to the first PX recovery unit 120, and the bottoms stream 114 containing $C_{9+}$ hydrocarbons may be further processed, such as in a transalkylation process, to produce xylenes or sent to the motor gasoline pool for use in fuels.

Figure 4A:
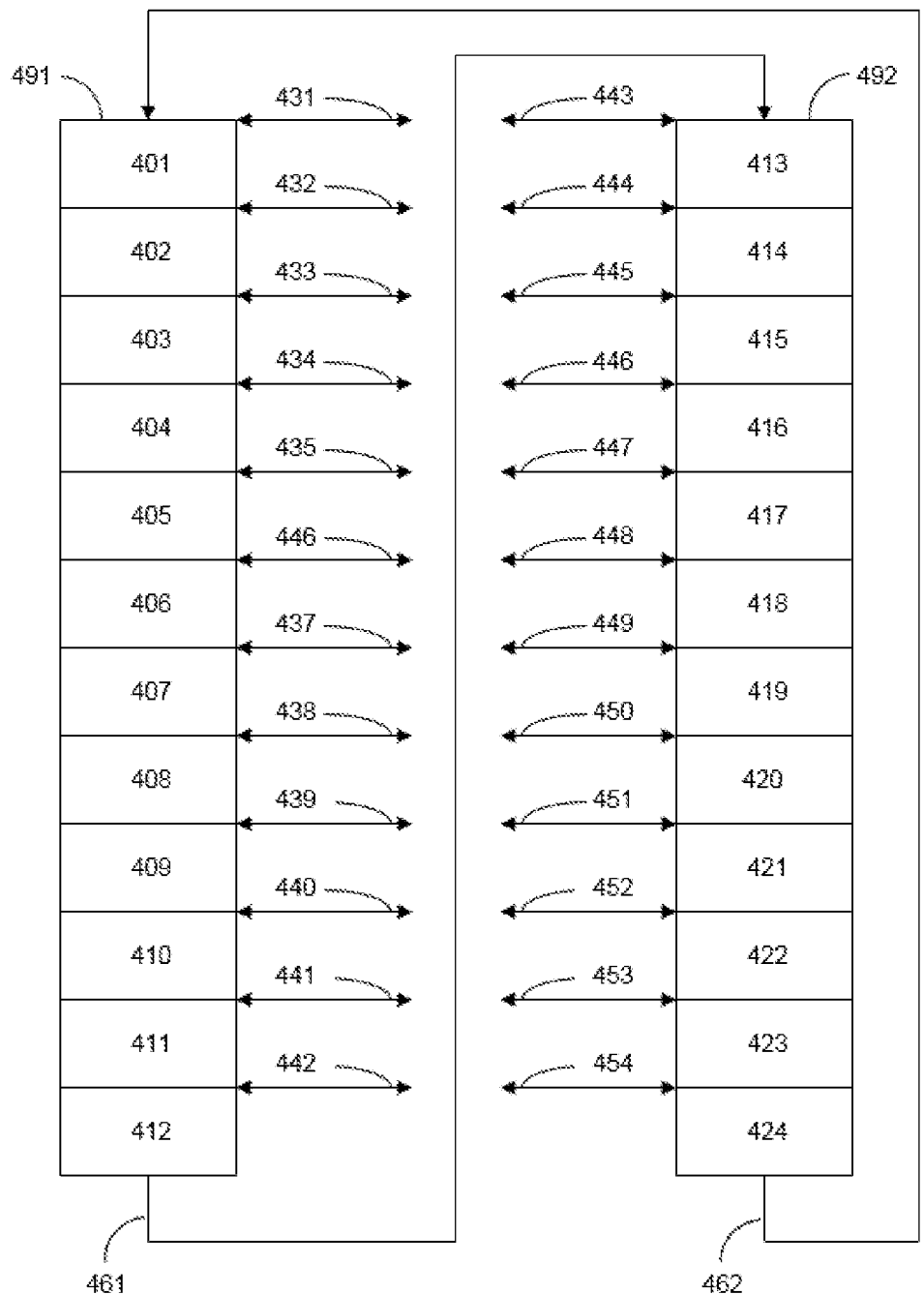
FIG. 4A illustrates a conventional simulated moving bed adsorption unit.

FIG. 4A illustrates a standard simulated moving bed apparatus with 24 adsorbent beds. This 24 bed configuration is particularly useful for separating one $C_8$ aromatic, such as PX, from a mixture of $C_8$ aromatics, such as a mixture of PX, MX, OX, and EB. A simulated moving bed adsorption unit uses a solid adsorbent which preferentially retains the PX in order to separate the PX from the rest of the mixture. The solid adsorbent is in the form of a simulated moving bed, where the bed of solid adsorbent is held stationary, and the locations at which the various streams enter and leave the bed are periodically moved. The adsorbent bed itself is usually a succession of fixed sub-beds. The shift in the locations of liquid input and output in the direction of the fluid flow through the bed simulates the movement of the solid adsorbent in the opposite direction.

In FIG. 4A, twelve adsorbent beds 401-412 are stacked in a first column 491 and another twelve adsorbent beds 413-424 are stacked in a second column 492. Conduits in fluid communication with a fluid distribution device are depicted by double arrows 431-454. The double arrows reflect the possibility of fluid flow either into or out of columns 491 and 492 during the multiple steps of the simulated moving bed process. For simplicity, the fluid distribution device is not shown in FIG. 4A. Also, not shown in FIG. 4A are fluid collection areas between beds. However, it will be understood that such collection areas, such as those represented as downcomers as described in U.S. Pat. No. 3,201,491, may be present in columns 491 and 492 of FIG. 1.

A circulating bulk fluid, which is taken from the bottom of column 492 and bed 424, is introduced into the top of column 491 and bed 401 through line 462 shown in FIG. 4A. The circulating bulk fluid flows in a downward direction through each of the beds of the first column 491 and is then transported to the top of the second column 492 through line 461. The circulating bulk fluid then flows in a downward direction through each of the beds of the second column 492.

Figure 4B:
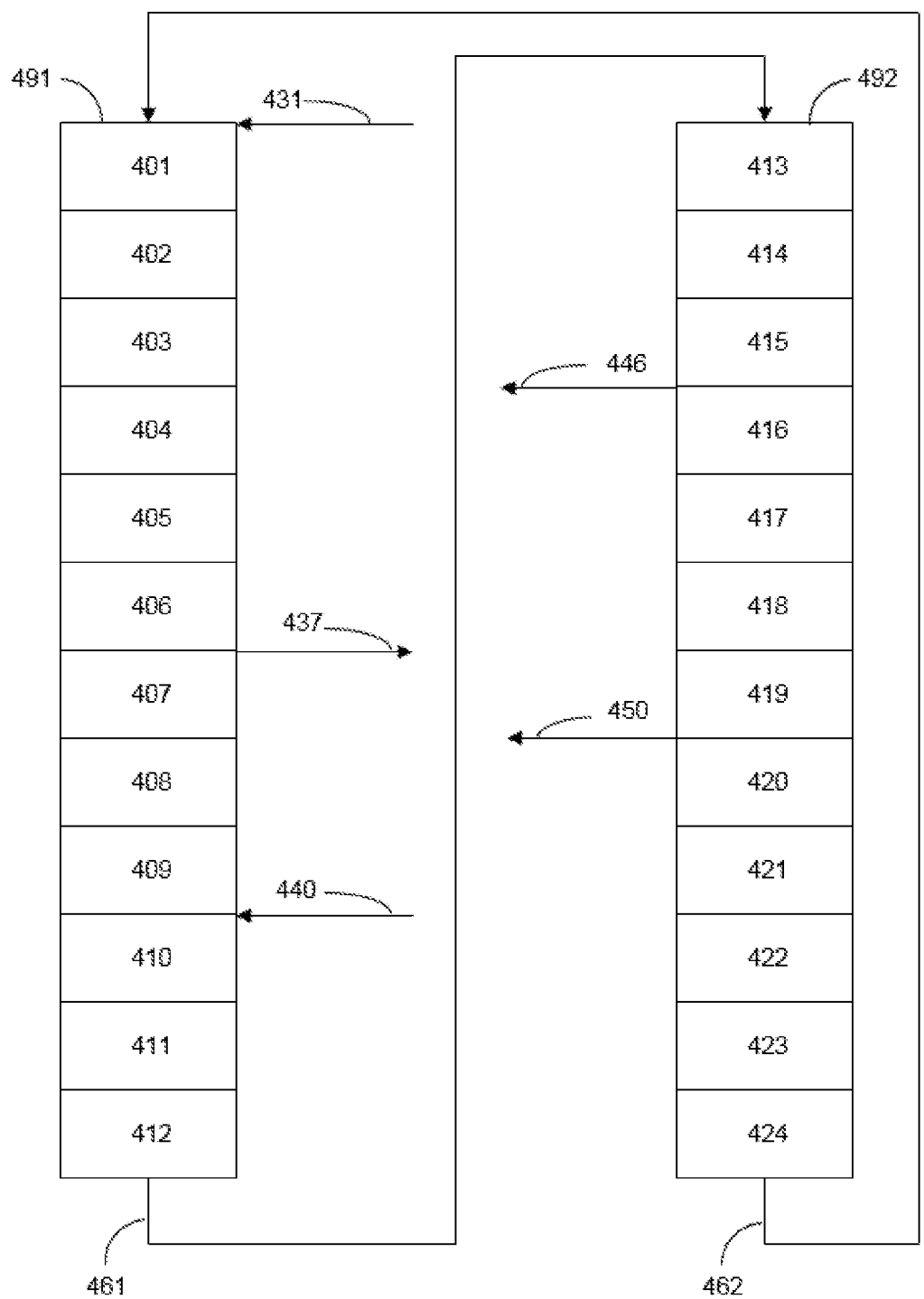
FIG. 4B illustrates a simulated moving bed adsorption unit as used in at least some of the embodiments disclosed herein.

FIG. 4B shows the flow of fluids through columns 491 and 492 during a single step of an adsorption cycle in accordance with at least some embodiments disclosed herein. The flow of fluids in FIG. 4B represents a standard simulated moving bed operation, where two extract streams are withdrawn. In particular, a PX-rich extract stream and an EB-rich extract stream is separated from a mixture comprising PX, MX, OX, and EB.

Numbered features in FIG. 4B correspond to numbered features in FIG. 4A. In FIG. 4B, the double arrows in FIG. 4A are replaced with single arrows to show the actual direction of flow of fluids during a single step in accordance with at least some embodiments disclosed herein.

The following steps occur at the same time in columns 491 and 492. Overhead stream 112 comprising $C_8$ hydrocarbons, which comprises a mixture of PX, MX, OX, and EB, is introduced into the top of bed 401 in column 491 via conduit 431. A first PX-depleted raffinate stream (e.g., stream 126 is FIGS. 2 and 3), which comprises a desorbent, MX, OX, and EB, is withdrawn from the top of bed 407 through conduit 437. A desorbent stream is introduced into the top of bed 410 through conduit 440. The desorbent may be, for example, PDEB, toluene, or tetralin. A first PX-rich extract stream (e.g., stream 122 in FIGS. 2 and 3), which comprises desorbent and PX, is withdrawn from the top of bed 416 through conduit 446, and an EB-rich extract stream (e.g., stream 124 in FIGS. 2 and 3), which comprises desorbent, EB, PX, MX, and OX is withdrawn from the top of bed 420 through conduit 450.

With respect to the direction of circulating bulk fluid (downward through column 491 and then downward through column 492), both the PX-rich extract stream and EB-rich extract stream are withdrawn at locations downstream of the desorbent introduction location and upstream of the feed introduction location. The EB-rich extract stream is withdrawn downstream of the PX-rich extract stream. The order of the net streams in this configuration (as shown in FIG. 4B) is feed introduction location, raffinate withdrawal location, desorbent introduction location, PX-rich extract withdrawal location, and EB-rich extract withdrawal location. The withdrawal locations for the PX-rich extract stream and EB-rich extract stream may be determined by one skilled in the art based on the adsorption profile. Generally the withdrawal location for the PX-rich extract stream is chosen to obtain a purity of at least 80 wt % PX, preferably at least 90 wt % PX, more preferably at least 95 wt % PX, and ideally at least 97 wt % PX, based on the total weight of the PX-rich product stream. As used herein, "purity" of a stream means the weight percentage of a certain component in the stream, excluding the desorbent. The EB-rich extract stream should be withdrawn at a location where the recovery of EB is at least 5 wt %, preferably at least 10 wt %, and more preferably at least 15 wt %, based on the total weight of EB in the hydrocarbon feed stream. As used herein, "recovery" of a component means the weight percentage of a certain component, based on the total amount of the component introduced into the system, in the hydrocarbon feed stream.

Referring again to FIGS. 2 and 3, the PX-depleted raffinate stream 126 may be separated in fractionation column 130 to produce PX-depleted stream 132 and desorbent stream 134. The desorbent stream 134 is recycled to the first PX recovery unit 120 and the PX-depleted stream 132 may be isomerized to produce more PX.

Because a significant amount of the EB from the first hydrocarbon feed 102 has been removed (at least enough to limit buildup in the isomerization loop) as a second extract stream (EB-rich extract stream 124) in the first simulated moving bed adsorption unit 120, at least a portion of, and preferably the entirety of, the PX-depleted stream 132 is sent to liquid phase isomerization unit 140. Avoiding vapor phase isomerization saves energy and capital, as liquid phase isomerization requires less energy and capital than the vapor phase isomerization process due to the requirement of vaporizing the PX-depleted stream and the use of hydrogen, which requires an energy- and capital-intensive hydrogen recycle loop. Liquid phase isomerization also reduces the destruction of xylene molecules into less valuable non-aromatics.

In the liquid phase xylene isomerization unit 140, the PX-depleted stream 132 is contacted with a xylene isomerization catalyst under at least partially liquid phase conditions effective to isomerize the PX-depleted stream 132 back towards an equilibrium concentration of the xylene isomers. Suitable conditions for the liquid phase isomerization include a temperature of from about 200° C. to about 540° C., preferably from about 230° C. to about 310° C., and more preferably from about 270° C. to about 300° C., a pressure of from about 0 to 6895 kPa(g), preferably from about 1300 kPa(g) to about 3500 kPa(g), a weight hourly space velocity (WHSV) of from 0.5 to 100 $hr^{-1}$, preferably from 1 to 20 $hr^{-1}$, and more preferably from 1 to 10 $hr^{-1}$. Generally, the conditions are selected so that at least 50 wt % of the $C_8$ aromatics would be expected to be in the liquid phase.

Any catalyst capable of isomerizing xylenes in the liquid phase can be used in the xylene isomerization unit, but in one embodiment the catalyst comprises an intermediate pore size zeolite having a Constraint Index between 1 and 12. Constraint Index and its method of determination are described in U.S. Pat. No. 4,016,218, which is incorporated herein by reference. Particular examples of suitable intermediate pore size zeolites include ZSM-5, ZSM-11, ZSM-12, ZSM-22, ZSM-23, ZSM-35, ZSM-48, and MCM-22, with ZSM-5 and ZSM-11 being particularly preferred, specifically ZSM-5. It is preferred that the acidity of the zeolite, expressed as its alpha value, be greater than 300, such as greater than 500, or greater than 1000. The alpha test is described in U.S. Pat. No. 3,354,078; in the Journal of Catalysis, Vol. 4, p. 527 (1965); Vol. 6, p. 278 (1966); and Vol. 61, p. 395 (1980), each incorporated herein by reference as to that description. The experimental conditions of the test used to determine the alpha values cited herein include a constant temperature of 538° C. and a variable flow rate as described in detail in the Journal of Catalysis, Vol. 61, p. 395. A preferred catalyst is described in U.S. Pat. No. 8,569,559, which is incorporated herein by reference.

The product of the liquid phase xylene isomerization process 140 is a first isomerized stream 142 having a higher PX concentration than the PX-depleted stream 132. The first isomerized stream 142 is then recycled to the first simulated moving bed adsorption unit 120 to recover additional PX and the process is repeated to generate a so-called xylene isomerization loop. Conducting xylenes isomerization under liquid phase conditions produces less $C_{9+}$ aromatics than xylenes isomerization under vapor phase conditions. Therefore, the isomerized stream 152 may be provided to the xylenes fractionation tower 110 at a higher tray location than an isomerized stream produced by vapor phase isomerization, yielding greater energy savings. Furthermore, a significant portion of the isomerized stream 142 may bypass the xylenes fractionation tower 110 and directly enter the first simulated moving bed adsorption unit 120, thereby saving energy by avoiding the re-fractionation altogether. Additionally, liquid phase isomerization reduces the amount of $C_{7-}$ hydrocarbons produced in the xylene isomerization loop, allowing for reduced use of a $C_{7-}$ distillation tower (unit 53 in FIG. 1), resulting in further energy savings. Exclusive use of liquid phase isomerization allows for elimination of the $C_{7-}$ distillation tower as shown in FIG. 2 and FIG. 3.

The first PX-rich extract stream 122 may be separated in a first extract column 150 to remove desorbent and produce a desorbent-free PX-rich extract stream 152. As used herein, "desorbent-free" means that the stream contains less than about 1 wt % desorbent, preferably less than 0.5 wt % desorbent. The desorbent stream 154 may be recycled to the first simulated moving bed adsorption unit 120. The desorbent-free PX-rich stream 152 may be further purified in a first finishing column 160 to remove contaminants such as toluene and water 164 and produce a first pure PX stream 162, which contains at least about 99.7 wt % PX.

The destination for the EB-rich extract stream 124 is dependent upon the amount of PX contained in the stream. Ideally, the withdrawal location for the EB-rich extract stream 124 is chosen to minimize the amount of PX contained in the EB-rich extract stream 124. If the amount of PX in the EB-rich extract stream 124 is sufficiently low, the EB-rich extract stream 124 may be sent to further processing, such as styrene production, or to the motor gasoline pool. While some PX may be sacrificed in this embodiment, the energy and cost benefits of not having a second separation step to further recover PX may outweigh the detriment of losing a minimal amount of PX. However, practically it may not be possible to withdraw the EB-rich extract stream 124 without a significant amount of PX, and the EB-rich extract stream 124 may be sent to a PX recovery unit, such as a second simulated moving bed adsorption unit or crystallization unit, to recover a second PX-rich extract stream. Optionally, the desorbent may be removed from the EB-rich extract stream 124 prior to the PX recovery unit.

In some embodiments, the first extract column 150 is a dividing wall column that accepts both the PX-rich extract stream 122 and the EB-rich extract stream 124. This dividing wall column may remove desorbent from both streams while keeping the light components of both feed streams separate. In addition, the dividing wall column in these embodiments may produce a common heavy product made up mostly of desorbent.

In the embodiment shown in FIG. 2, the EB-rich extract stream 124 is sent to a second simulated moving bed adsorption unit 220 to recover the PX in the EB-rich extract stream 124. The EB-rich extract stream 124 may comprise the entirety of the feed stream to the second simulated moving bed adsorption unit 220 or it may be combined with a second hydrocarbon feed stream 202 prior to the second simulated moving bed adsorption unit 220. The second hydrocarbon feed stream 202 may be the same as the first hydrocarbon feed stream 102 or be another hydrocarbon stream with the characteristics as described above in relation to the first hydrocarbon feed stream 102. Depending on the composition of the hydrocarbon feed 102, one or more initial separation steps that serve to remove $C_{7-}$ and $C_{9+}$ hydrocarbons from the feed may occur. Generally the initial separation steps may include fractional distillation, crystallization, adsorption, a reactive separation, a membrane separation, extractions or any combination thereof. In embodiments, shown in FIG. 2, before going to the second simulated moving bed 220, the second hydrocarbon feed 202 is passed through a xylenes fractionation tower 210 prior to passing to the PX recovery unit 220. The xylenes fractionation tower 210 produces an overhead stream 212 comprising $C_8$ hydrocarbons and a bottoms stream 214 containing $C_{9+}$ hydrocarbons. The overhead stream 212 comprising $C_8$ hydrocarbons is sent to the second PX recovery unit 220, and the bottoms stream 214 containing $C_{9+}$ hydrocarbons may be further processed, such as in a transalkylation process, to produce xylenes or sent to the motor gasoline pool for use in fuels.

The second simulated moving bed adsorption unit 220 produces a second PX-rich extract stream 222 and a PX-depleted raffinate stream 224. The second simulated moving bed adsorption unit 220 may contain the same adsorbent as the first simulated moving bed adsorption unit 120, or it may contain a different adsorbent than the second simulated moving bed adsorption unit 120 that provides better separation between EB and PX. In particular, in at least some embodiments the adsorbent of the second simulated moving bed adsorption unit 220 may have a higher affinity for EB than PX. The second simulated moving bed adsorption unit 220 may be a second unit such as that shown in FIG. 4A, or a conventional simulated moving bed adsorption unit having 24 adsorbent beds divided into two columns of 12 adsorbent beds each, such as that shown in FIG. 4A, may be retrofitted such that the first column of 12 adsorbent beds functions as the first simulated moving bed unit 120 and the second column of 12 adsorbent beds functions as the second simulated moving bed unit 220.

Figure 7:
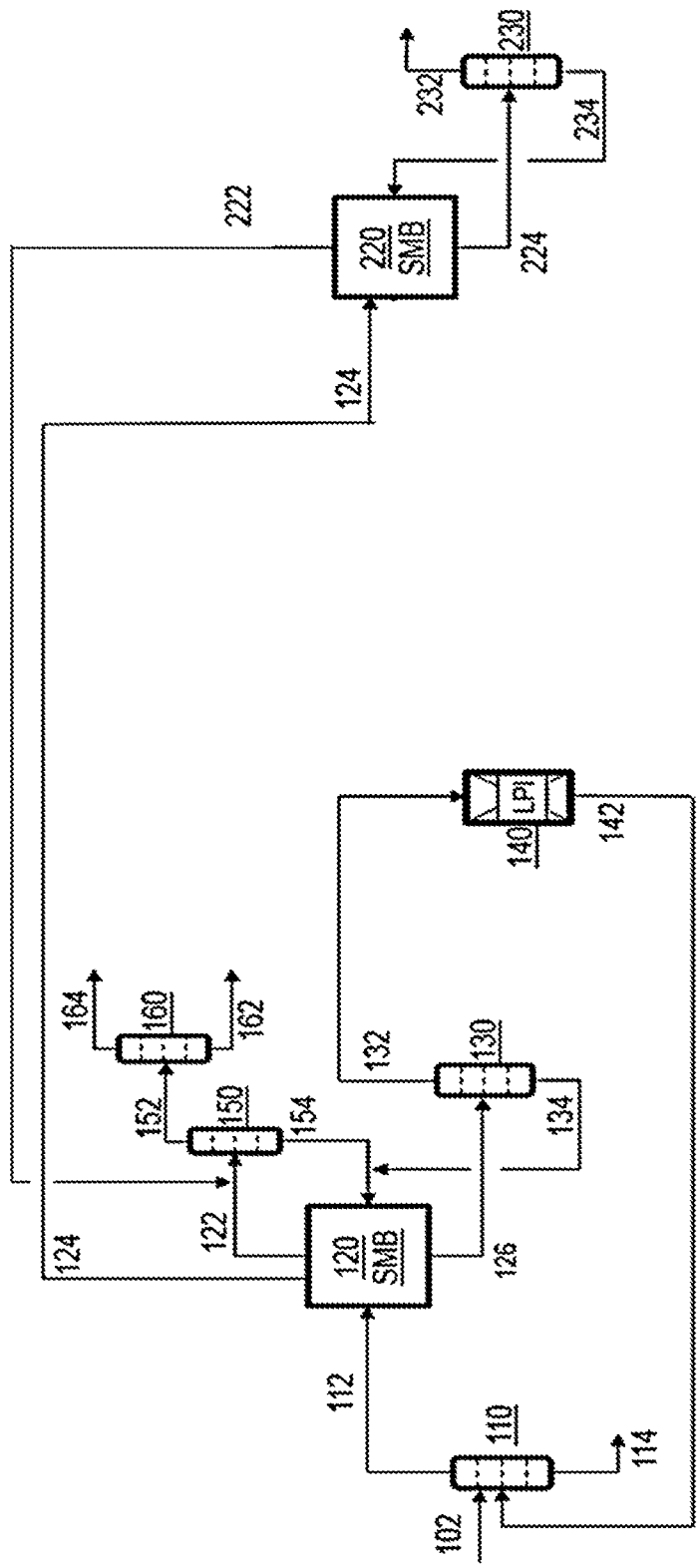
FIG. 7 illustrates a PX production and extraction process in accordance with at least some embodiments disclosed herein.

The second PX-rich extract stream 222 may be separated in a second extract column 250 to remove desorbent and produce a desorbent-free PX-rich extract stream 252. The desorbent stream 254 may be recycled to the second simulated moving bed adsorption unit 220. The desorbent-free PX-rich stream 252 may be further purified in a second finishing column 260 to remove contaminants such as toluene and water 264 and produce a second pure PX stream 262, which contains at least about 99.7 wt % PX. In another embodiment (such as the embodiment of FIG. 7), the second PX-rich extract stream 222 is provided to the first extract column 150 and subsequently to the first finishing column 160, eliminating the need for a second extract column 250 and second finishing column 260. In addition, in the embodiment of FIG. 7 vapor phase isomerization unit 240, xylenes fractionation tower 210, fractionation column 270 (discussed below) are each also omitted; however, it should be appreciated that these components may be included in other embodiments that route PX-rich extract stream 222 to the first extract column as shown in FIG. 7.

Referring again to FIG. 2, the PX-depleted raffinate stream 224 may be separated in fractionation column 230 to produce PX-depleted stream 232 and desorbent stream 234. The desorbent stream 234 is recycled to the second PX recovery unit 220 and the PX-depleted stream 232 may be isomerized to produce more PX. Because the PX-depleted raffinate stream 224 contains a significant amount of EB, vapor phase isomerization must be used in some embodiments to convert the EB therein to limit a buildup of EB in the process. At least a portion of, and preferably the entirety of, the PX-depleted stream 232 then passes to vapor phase isomerization unit 240. In other embodiments (e.g., the embodiment of FIG. 7), the PX-depleted raffinate stream 232, which includes a significant amount of EB is simply emitted from the process and is either sold or utilized in other processes as an EB-containing stream.

In the vapor phase xylene isomerization unit 240, the PX-depleted stream 232 is contacted with a xylene isomerization catalyst under at least partially vapor phase conditions effective to isomerize the PX-depleted stream 232 back towards an equilibrium concentration of the xylene isomers. There are generally two types of vapor phase isomerization catalysts—one that dealkylates EB to produce benzene and ethylene and isomerizes the xylene isomers, and one that isomerizes the four different C8 aromatic compounds, including EB, to their equilibrium concentrations. Either catalyst may be used for the vapor phase isomerization unit 240.

In one embodiment, the PX-depleted stream 232 is subjected to xylenes isomerization in which the EB in the stream can be dealkylated to produce benzene. In this embodiment, where the EB is removed by cracking/disproportionation, the PX-depleted $C_8$ stream is conveniently fed to a multi-bed reactor comprising at least a first bed containing an EB conversion catalyst and a second bed downstream of the first bed and containing a xylene isomerization catalyst. The beds can be in the same or different reactors. Alternatively, the EB conversion catalyst and xylene isomerization catalyst may be contained in a single bed reactor.

The EB conversion catalyst typically comprises an intermediate pore size zeolite having a Constraint Index ranging from 1 to 12, a silica to alumina molar ratio of at least about 5, such as at least about 12, for example at least 20, and an alpha value of at least 5, such as 75 to 5000. Constraint Index and its method of determination are disclosed in U.S. Pat. No. 4,016,218, which is herein incorporated by reference, whereas the alpha test is described in U.S. Pat. No. 3,354,078 and in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the Journal of Catalysis, Vol. 61, p. 395. Higher alpha values correspond with a more active cracking catalyst.

Examples of suitable intermediate pore size zeolites include ZSM-5 (U.S. Pat. Nos. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57; ZSM-58; EU-1; and mordenite. The entire contents of the above references are incorporated by reference herein. Preferred zeolites are ZSM-5, ZSM-12 or EU-1.

The zeolite employed in EB conversion catalyst typically has a crystal size of at least 0.2 microns and exhibits an equilibrium sorption capacity for xylene, which can be either para, meta, ortho, or a mixture thereof, of at least 1 gram per 100 grams of zeolite measured at 120° C. and a xylene pressure of 4.5±0.8 mm of mercury and an OX sorption time for 30 percent of its equilibrium OX sorption capacity of greater than 1200 minutes (at the same conditions of temperature and pressure). The sorption measurements may be carried out gravimetrically in a thermal balance. The sorption test is described in U.S. Pat. Nos. 4,117,026; 4,159,282; 5,173,461; and Re. 31,782, each of which is incorporated by reference herein.

The zeolite used in the EB conversion catalyst may be self-bound (no binder) or may be composited with an inorganic oxide binder, with the zeolite content ranging from between about 1 to about 99 percent by weight and more usually in the range of about 10 to about 80 percent by weight of the dry composite, e.g., about 65% zeolite with about 35% binder. Where a binder is used, it is preferably non-acidic, such as silica. Procedures for preparing silica bound ZSM-5 are described in U.S. Pat. Nos. 4,582,815; 5,053,374; and 5,182,242, incorporated by reference herein.

In addition, the EB conversion catalyst typically comprises from about 0.001 to about 10 percent by weight, e.g., from about 0.05 to about 5 percent by weight, e.g., from about 0.1 to about 2 percent by weight of a hydrogenation/dehydrogenation component. Examples of such components include the oxide, hydroxide, sulfide, or free metal (i.e., zero valent) forms of Group VIIIA metals (i.e., Pt, Pd, Ir, Rh, Os, Ru, Ni, Co, and Fe), Group VIIA metals (i.e., Mn, Tc, and Re), Group VIA metals (i.e., Cr, Mo, and W), Group VB metals (i.e., Sb and Bi), Group IVB metals (i.e., Sn and Pb), Group IIIB metals (i.e., Ga and In), and Group IB metals (i.e., Cu, Ag and Au). Noble metals (i.e., Pt, Pd, Ir, Rh, Os and Ru) are preferred hydrogenation/dehydrogenation components. Combinations of catalytic forms of such noble or non-noble metal, such as combinations of Pt with Sn, may be used. The metal may be in a reduced valence state, e.g., when this component is in the form of an oxide or hydroxide. The reduced valence state of this metal may be attained, in situ, during the course of a reaction, when a reducing agent, such as hydrogen, is included in the feed to the reaction.

The xylene isomerization catalyst employed in this embodiment typically comprises an intermediate pore size zeolite, e.g., one having a Constraint Index between 1 and 12, specifically ZSM-5. The acidity of the ZSM-5 of this catalyst, expressed as the alpha value, is generally less than about 150, such as less than about 100, for example from about 5 to about 25. Such reduced alpha values can be obtained by steaming. The zeolite typically has a crystal size less than 0.2 micron and an OX sorption time such that it requires less than 50 minutes to sorb OX in an amount equal to 30% of its equilibrium sorption capacity for OX at 120° C. and a xylene pressure of 4.5+0.8 mm of mercury. The xylene isomerization catalyst may be self-bound form (no binder) or may be composited with an inorganic oxide binder, such as alumina. In addition, the xylene isomerization catalyst may contain the same hydrogenation/dehydrogenation component as the EB conversion catalyst.

Using the catalyst system described above, EB cracking/disproportionation and xylene isomerization are typically effected at conditions including a temperature of from about 400° F. to about 1,000° F. (204 to 538° C.), a pressure of from about 0 to about 1,000 psig (100 to 7,000 kPa), a weight hourly space velocity (WHSV) of between about 0.1 and about 200 hr−1, and a hydrogen, $H_2$ to hydrocarbon, HC, molar ratio of between about 0.1 and about 10. Alternatively, the conversion conditions may include a temperature of from about 650° F. and about 900° F. (343 to 482° C.), a pressure from about 50 and about 400 psig (446 to 2,859 kPa), a WHSV of between about 3 and about 50 hr−1 and a $H_2$ to HC molar ratio of between about 0.5 and about 5. The WHSV is based on the weight of catalyst composition, i.e., the total weight of active catalyst plus, if used, binder therefor.

In another embodiment, the PX-depleted stream 232 is subjected to EB isomerization to produce a stream containing the $C_8$ aromatic compounds in equilibrium concentrations.

Typically, the EB isomerization catalyst comprises an intermediate pore size molecular sieve having a Constraint Index within the approximate range of 1 to 12, such as ZSM-5 (U.S. Pat. No. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57; and ZSM-58. Alternatively, the xylene isomerization catalyst may comprise a molecular sieve selected from MCM-22 (described in U.S. Pat. No. 4,954,325); PSH-3 (described in U.S. Pat. No. 4,439,409); SSZ-25 (described in U.S. Pat. No. 4,826,667); MCM-36 (described in U.S. Pat. No. 5,250,277); MCM-49 (described in U.S. Pat. No. 5,236,575); and MCM-56 (described in U.S. Pat. No. 5,362,697). The molecular sieve may also comprise a EUO structural type molecular sieve, with EU-1 being preferred, or mordenite. A preferred molecular sieve is one of the EUO structural type having a Si/Al ratio of about 10-25, as disclosed in U.S. Pat. No.

7,893,309. The entire contents of the above references are incorporated by reference herein.

It may be desirable to combine the molecular sieve of the xylene isomerization catalyst with another material resistant to the temperature and other conditions of the process. Such matrix materials include synthetic or naturally occurring substances as well as inorganic materials such as clay, silica, and/or metal oxides (such as titanium oxide or boron oxide). The metal oxides may be naturally occurring or in the form of gelatinous precipitates or gels including mixtures of silica and metal oxides. Naturally occurring clays, which can be composited with the molecular sieve, include those of the montmorillonite and kaolin families, which families include the subbentonites and the kaolins commonly known as Dixie, McNamee, Ga., and Florida clays or others in which the main mineral constituent is halloysite, kaolinite, dickite, nacrite, or anauxite. Such clays can be used in the raw state as originally mined or initially subjected to calcination, acid treatment, or chemical modification.

In addition to the foregoing materials, the molecular sieve may be composited with a porous matrix material, such as alumina, zirconia, silica-alumina, silica-magnesia, silica-zirconia, silica-thoria, silica-berylia, silica-titania, aluminum phosphates, titanium phosphates, zirconia phosphates, as well as ternary compounds such as silica-alumina-thoria, silica-alumina-zirconia, silica-alumina-magnesia, and silica-magnesia-zirconia. A mixture of these components could also be used. The matrix may be in the form of a cogel. The relative proportions of molecular sieve component and inorganic oxide gel matrix on an anhydrous basis may vary widely with the molecular sieve content ranging from between about 1 to about 99 percent by weight and more usually in the range of about 10 to about 80 percent by weight of the dry composite.

The EB isomerization catalyst also comprises at least one metal from Group VIII of the periodic table of the elements and optionally at least one metal selected from metals from Groups IIIA, IVA, and VIIB. The Group VIII metal present in the catalyst used in the isomerization process is selected from iron, cobalt, nickel, ruthenium, rhodium, palladium, osmium, iridium, and platinum, preferably from the noble metals and highly preferably from palladium and platinum. More preferably, the Group VIII metal is platinum. The metal selected from groups IIIA, IVA, and VIIB which are optionally present is selected from gallium, indium, tin, and rhenium, preferably from indium, tin, and rhenium.

The conditions employed in the EB isomerization process generally include a temperature of from 300 to about 500° C., preferably from about 320 to about 450° C. and more preferably from about 340 to about 430° C.; a partial pressure of hydrogen from about 0.3 to about 1.5 MPa, preferably from about 0.4 to about 1.2 MPa, and more preferably from about 0.7 to about 1.2 MPa; a total pressure of from about 0.45 to about 1.9 MPa, preferably from about 0.6 to about 1.5 MPa; and a weight hourly space velocity (WHSV) of between about 0.25 and about 30 $hr^{-1}$, preferably between about 1 and about 10 $hr^{-1}$ and more preferably between about 2 and about 6 $hr^{-1}$.

The product of the vapor phase xylene isomerization process 240 is a second isomerized stream 242 having a higher PX concentration than the second PX-depleted raffinate stream 224 or the second PX-depleted stream 232. The second isomerized stream 242 is then recycled to one or both of the first simulated moving bed adsorption unit 120 and second simulated moving bed adsorption unit 220. Prior to the first or second simulated moving bed adsorption units 120, 220, the second isomerized stream 242 may be sent through fractionation column 270 to remove the $C_{7-}$ hydrocarbons 274 and produce a $C_{8+}$ hydrocarbon stream 272, which may be processed through the xylenes fractionation column 110 or 210.

In an embodiment in which the EB-rich extract stream 124 comprises the entirety of the feed stream to the second simulated moving bed adsorption unit 220 (not shown), the PX-depleted raffinate stream 224 may be essentially free of other xylene isomers. Thus, the fractionation column 230 would produce an overhead stream that is essentially pure EB, which would then be available for the motor gasoline pool or other refinery processes. In this embodiment, there is no need for any isomerization in of the raffinate stream of the second simulated moving bed adsorption unit, eliminating the need for vapor phase isomerization.

In the embodiment shown in FIG. 3, the EB-rich extract stream 124 is sent to a crystallization unit 300 to recover the PX in the EB-rich extract stream 124. The crystallization unit 300 produces a second PX-rich extract stream 302 and an EB-rich liquid product 304. The second PX-rich extract stream 302 may be purified using the conventional crystallization equipment or may be sent to the first extract column 150 and subsequently to the first finishing column 160, eliminating the need for a second extract column and second finishing column. The EB-rich liquid product 304 may be sent to a refinery stream or may be further purified for downstream processes.

EXAMPLES

In the Examples that follow, a computer model is used to simulate the separation of PX from other $C_8$ aromatics in the first simulated moving bed unit 120 as shown in FIGS. 2 and 3. The unit comprises two columns, as shown in FIG. 4A, in fluid communication with a rotary valve device. Each column comprises twelve adsorbent bed chambers, stacked one on top of the other, containing an adsorbent. For the purposes of explanation, these beds are identified as beds 101 to 124. The number of beds described in each zone is for illustrative purposes and the number of beds may be varied without changing the concepts described herein.

In the first column, the beds are stacked such that fluid introduced into the top of the first column flows downward through the first bed (i.e., bed 101) and then through the beds below to the last bed (i.e., bed 112) in the first column. Fluid from the bottom of the first column then flows to the top of the second column where it flows downward through the beds (i.e., beds 113-124). Fluid from the bottom of the second column then flows to the top of the first column to complete a loop of circulating bulk fluid throughout the columns.

The initial introduction of feed may take place in any of the beds of the apparatus. For example, feed may be introduced to the first bed in the first column. The feed is primarily composed of a mixture of $C_8$ aromatics. The feed may also include small amounts of impurities including toluene and paraffins. The feed may be a mixture of product streams from a reforming process, a transalkylation process, and an isomerization process.

When a steady state operation of the simulated moving bed (SMB) unit is achieved, the beds of the apparatus may be described in terms of four sub-zones, i.e., a desorption sub-zone, a purification or rectification sub-zone, an adsorption sub-zone, and a buffer sub-zone. In a standard SMB unit, (1) the desorption sub-zone may include the bed to which a desorbent stream is introduced and six beds downstream from this bed terminating in the bed from which the extract stream is withdrawn, (2) the purification sub-zone may include nine beds immediately downstream of desorption sub-zone, terminating with the bed immediately upstream from the bed to which feed is introduced, (3) the adsorption sub-zone may include the bed to which feed is introduced and six beds immediately downstream of the purification sub-zone terminating in the bed from which a raffinate stream is withdrawn, and (4) the buffer sub-zone may include three beds immediately downstream from the purification sub-zone and terminating in the bed immediately upstream from the desorption sub-zone. The number of beds in each zone may vary from the numbers described above.

The raffinate and extract streams may pass through conduits and through a rotary valve device. These streams may then be distilled to separate desorbent from $C_8$ aromatics. A PX product may be recovered from the distillation of the extract stream. MX, OX, and EB obtained by distillation of the raffinate stream may be passed to an isomerization unit to convert a portion of these $C_8$ aromatics to PX, and the isomerized $C_8$ aromatics may then be used as a portion of the feed to the adsorption process. Desorbent recovered by distillation of the extract and raffinate streams may be recycled to the adsorption process.

Parameters for Examples 1 and 2

In Examples 1 and 2 which follow, an SMB model that consists of 24 beds (length 1.135 m, cross-sectional area 13.3 m²) was employed. A mixture of $C_8$ aromatics (PX, OX, MX, and EB) and desorbent (PDEB) was assumed to be fed to the unit. Two extract streams, a PX-rich extract stream, herein referred to as Extract1, and an EB-rich extract stream, herein referred to as Extract2, were withdrawn at locations between the introduction locations of the desorbent and the feed, i.e., in the purification zone.

The zone configuration is consistent in this study. For an SMB with 24 beds, the zone configuration is fixed to 6:4:5:6:3 (i.e., six beds between desorbent and Extract1, four beds between Extract1 and Extract2, five beds between Extract2 and feed, six beds between feed and raffinate, and three bed between raffinate and desorbent).

Consistent with M. Minceva, and A. E. Rodrigues, 'Modeling and Simulation of a Simulated Moving Bed for the Separation of P-Xylene', *Industrial & Engineering Chemistry Research*, 41 (2002), 3454-61, the following assumptions are made: (1) isothermal, isobaric operation; (2) constant velocity within each zone; (3) solid phase concentration is homogeneous throughout adsorbent particles; and (4) the mass transfer between the liquid and adsorbent phases is described by the linear driving force (LDF) model.

Based on these assumptions, mass balance equations can be written as:

$$\frac{\partial C_{ik}(z,t)}{\partial t} = \mathcal{D}_{LK}(t)\frac{\partial^2 C_{ik}(z,t)}{\partial z^2} - v_k^*(t)\frac{\partial C_{ik}(z,t)}{\partial z} - \frac{(1-\varepsilon)}{\varepsilon}\frac{\partial q_{ik}(z,t)}{\partial t}$$

where i is the index for components (i=PX, MX, OX, EB, PDEB); k is the index for columns (k=1 ... $N_{bed}$, where $N_{bed}$ is the total number of beds); C is the bulk liquid concentration $$\left(\text{unit}\frac{\text{kg}}{\text{m}^3}\right);$$

q is the adsorbate concentration $$\left(\text{unit}\frac{\text{kg}}{\text{m}^3}\right);$$

$\varepsilon$ is the overall porosity; $\mathcal{D}$ is the axial dispersion coefficient; and $v_k^*$ is the interstitial velocity in columns.

This mass balance equation describes the change of bulk liquid concentration at a specific position inside of a column (first term) with respect to dispersion (second term), convection (third term), and adsorption/desorption process (fourth term).

The LDF model is written as:

$$\frac{\partial q_{ik}(z,k)}{\partial t} = k(q_{ik}^*(z,t) - q_{ik}(z,t))$$

where q* is the adsorbate concentration in equilibrium with the liquid phase $$\left(\text{unit}\frac{\text{kg}}{\text{m}^3}\right).$$

The LDF model describes the mass flux into the solid phase. The adsorbate concentration in equilibrium with the liquid phase can be obtained from an adsorption isotherm.

At the node between columns, the mass balance is calculated by subtracting outlet flow rates and adding inlet flow rates:

$$F_{k+1} = F_k + F_{Feed,k} + F_{desorbent,k} - F_{raffinate,k} - F_{extract1,k} - F_{extract2,k}$$

For columns that are not connected to inlet or outlet streams, $F_{Feed,k}$ or $F_{desorbent,k}$ or $F_{raffinate,k}$ or $F_{extract1,k}$ or $F_{extract2,k}$ is zero.

The CSS constraints are given as:

$$C_{k+1}(z,t_{end}) = C_k(z,t_0)$$

where $t_{end}$ is the time at the end of a step, and to is the beginning of a step. Here, stepwise symmetry is assumed, where every step is identical.

Model parameters were taken from the literature, in particular, from M. Minceva, and A. E. Rodrigues, 'Modeling and Simulation of a Simulated Moving Bed for the Separation of P-Xylene', *Industrial & Engineering Chemistry Research*, 41 (2002), 3454-61. Model parameters are summarized in Table 1.

TABLE 1

| SMB unit Geometry | Model Parameter |
|---|---|
| $L_c$ = 113.5 cm | $P_e = v_k L_k / D_{Lk}$ = 2000 |
| $d_c$ = 411.7 cm | k = 2 min$^{-1}$ |
| $V_c$ = 15.1 × 10$^6$ cm$^3$ | $d_p$ = 0.092 cm |
| No. of Columns = 24 | $\varepsilon$ = 0.39 |
| Configuration = 6-9-6-3 | $\rho$ = 1.39 g/cm$^3$ |
| | $q_{mPX(MX,OX,EB)}$ = 130.3 mg/g |
| | $K_{PX}$ = 1.0658 cm$^3$/mg |
| | $K_{MX}$ = 0.2299 cm$^3$/mg |
| | $K_{OX}$ = 0.1884 cm$^3$/mg |
| | $K_{EB}$ = 0.3067 cm$^3$/mg |
| | $q_{mPDEB}$ = 107.7 mg/g |
| | $K_{PDEB}$ = 1.2935 cm$^3$/mg |

The mass transfer coefficient was changed from 2 min$^{-1}$ to 0.75 min$^{-1}$.

The optimization problem was formulated as follows:
Objective function: maximize $F_{Feed}$
Decision variables: $F_1$, $F_2$, $F_3$, $F_4$, $F_5$, $t_{st}$
  where $F_j$'s are zone flow rates, and $t_{st}$ is the step time
Main Constraint: Extract1 purity (PX)≥99.7%
  Extract(1+2) recovery (PX)≥97.0%

The model was discretized into a set of algebraic differential equations by applying the center finite difference method (CFDM) to the spatial domain and orthogonal collocation finite element method (OCFEM) to the temporal domain respectively. The discretized problem was solved by an interior-point optimization algorithm, IPOPT.

Example 1

In this Example, additional constraints were imposed to ensure 15 wt % of the total amount of EB fed into the SMB system was recovered in the EB-rich extract stream (Extract2), and less than 1.0 wt % of the total OX and MX in the feed were recovered in Extract2. At least 15 wt % EB recovery in Extract2 minimizes EB build up in the xylene loop using liquid phase isomerization, allowing for significant energy savings by eliminating vapor phase isomerization. The corresponding EB composition in the feed to the SMB system increases to 14 wt % due to EB recycle from the isomerization units.

Figure 5:
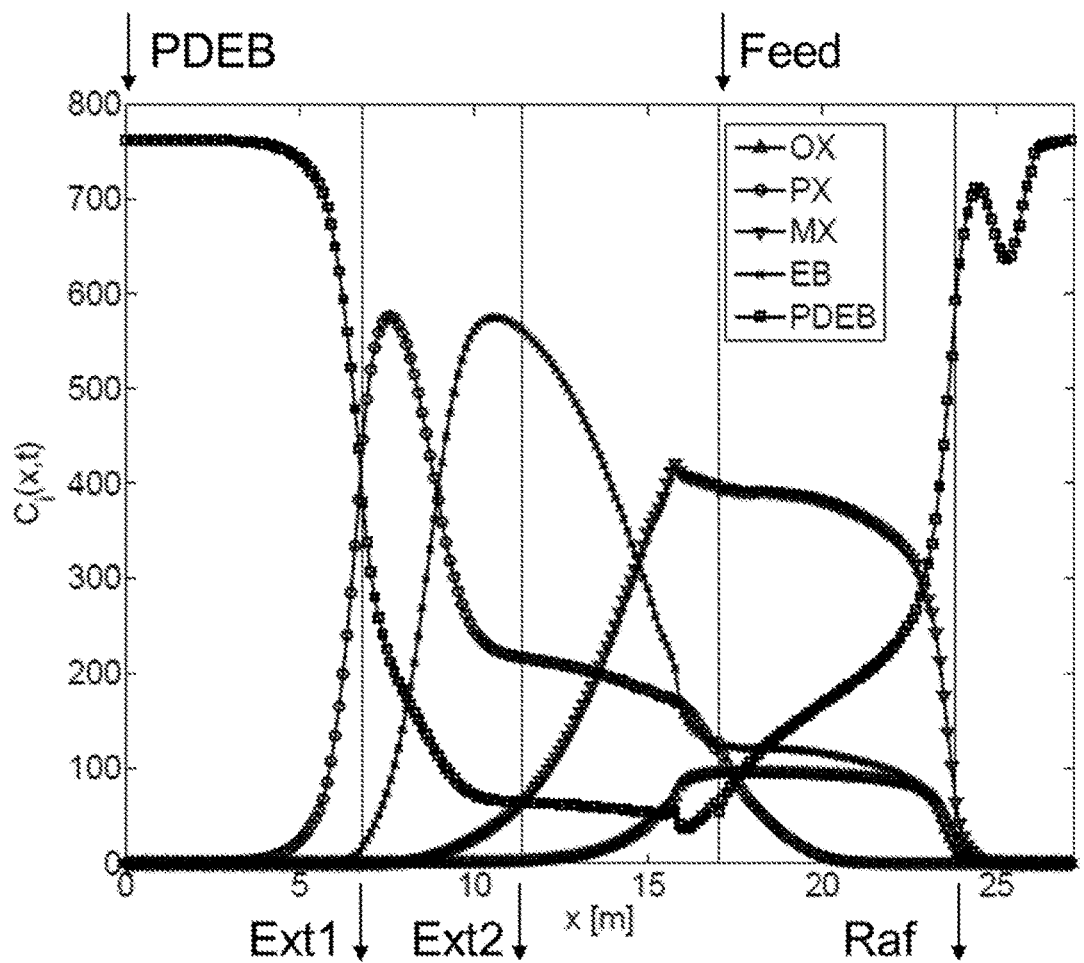
FIGS. 5 and 6 depict the concentration profiles of each component inside a first simulated moving bed unit of at least some of the embodiments disclosed herein.

FIG. 5 shows the concentration profile within the SMB system at the beginning of a step. The system is divided into five zones based on the two inlet streams and three outlet streams. The locations of the feed and desorbent inlets and raffinate and extract outlets are shown with arrows. The PX-rich extract stream (Extract1) and EB-rich extract stream (Extract2) are withdrawn from the upstream of the feed location while the raffinate stream is withdrawn from the downstream side of the feed location.

Table 2 shows the optimized mass flow rates of each component in the product outlets. The amount of PDEB has been unevenly split among the outlet streams. The EB-rich extract (Extract2) recovers only 1.3 wt % of the total PDEB in the SMB system. Thus, the PDEB may not need to be removed from the EB-rich extract (Extract2) prior to the PX recovery unit, eliminating the requirement of an additional fractionating tower.

TABLE 2

|  | OX | PX | MX | EB | PDEB |
|---|---|---|---|---|---|
| Feed (kg/min) | 241.5 | 448.8 | 945.2 | 266.2 | 0 |
| Desorbent (kg/min) | 0 | 0 | 0 | 0 | 1543 |
| Raffinate (kg/min) | 241 | 13.5 | 934.5 | 225.3 | 1060.6 |
| Extract 1 (kg/min) | 0.01 | 409 | 0.04 | 0.75 | 464 |
| Extract 2 (kg/min) | 0.22 | 27.8 | 9.43 | 39.8 | 19.3 |

Table 3 shows the purity and recovery obtained in all of the product outlets. The PX-rich extract stream (Extract1) recovers 91.1 wt % of PX with 99.8 wt % purity. The EB-rich extract stream (Extract2) recovers an additional 6.2 wt % of PX to ensure an overall recovery of PX of more than 97 wt %. The purity values of PX and EB in the EB-rich extract stream (Extract2) are 28.8 wt % and 41.3 wt %. This EB-rich extract stream (Extract2) can be either fed to a downstream SMB or a crystallizer to obtain pure PX and EB fractions. The desorbent to feed ratio required in this example is 0.81, which is less than required in a conventional Parex system, meaning the benefits of this multiple-extract scheme may come without increasing the energy consumption.

TABLE 3

|  | OX | PX | MX | EB |
|---|---|---|---|---|
| Raffinate purity (wt %) | 17 | 0.95 | 66.1 | 15.9 |
| Raffinate recovery (wt %) | 99.8 | 3 | 98.9 | 84.6 |
| Extract 1 purity (wt %) | 0 | 99.8 | 0.01 | 0.18 |
| Extract 1 recovery (wt %) | 0 | 91.1 | 0 | 0.28 |
| Extract 2 purity (w/PDEB) (wt %) | 0.22 | 28.8 | 9.8 | 41.3 |
| Extract 2 recovery (w/PDEB) (wt %) | 0.1 | 6.2 | 1 | 15 |

Example 2

In this Example, additional constraints were imposed to ensure 25 wt % of the total amount of EB fed into the SMB system was recovered in the EB-rich extract stream (Extract2), and less than 2.5 wt % of the total OX and MX in the feed were recovered in Extract2. At least 15 wt % EB recovery in Extract2 minimizes EB build up in the xylene loop using liquid phase isomerization, allowing for significant energy savings by eliminating vapor phase isomerization. The corresponding EB composition in the feed to the SMB system increases to 14 wt % due to EB recycle from the isomerization units.

Figure 6:
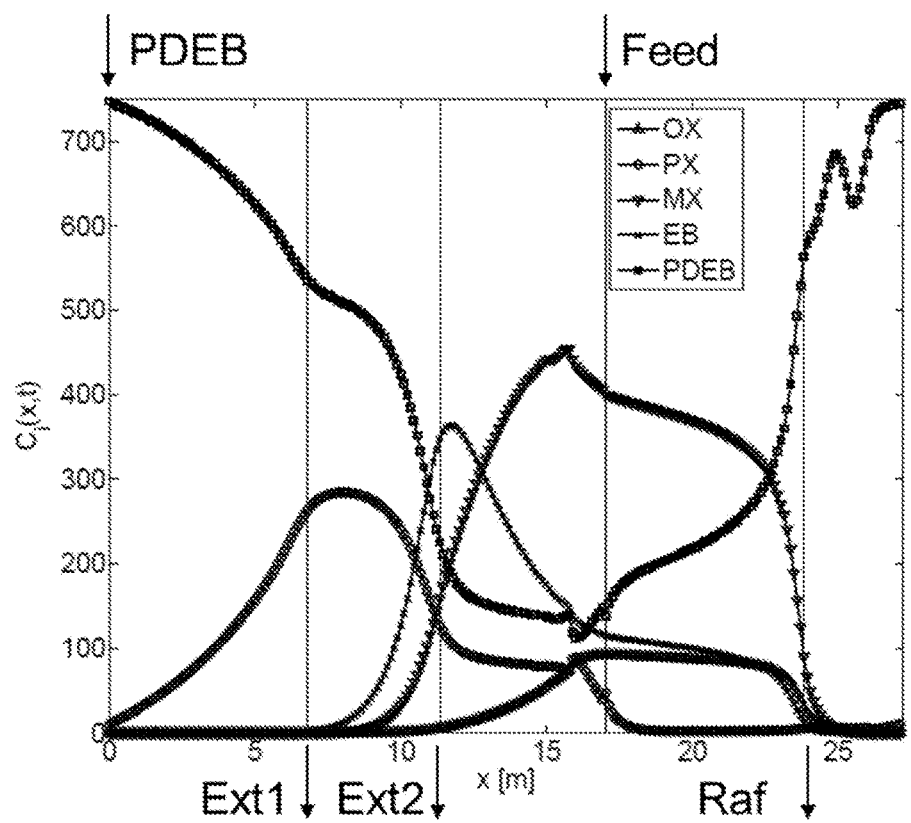

FIG. 6 shows the concentration profile within the SMB system at the beginning of a step. The system is divided into five zones based on the two inlet streams and three outlet streams. The locations of the feed and desorbent inlets and raffinate and extract outlets are shown with arrows. The PX-rich extract stream (Extract1) and EB-rich extract stream (Extract2) are withdrawn from the upstream of the feed location while the raffinate stream is withdrawn from the downstream side of the feed location.

Table 4 shows the optimized mass flow rates of each component in the product outlets. The amount of PDEB has been unevenly split among the outlet streams. The EB-rich extract (Extract2) recovers only 3.5 wt % of the total PDEB in the SMB system. Thus, the PDEB may not need to be removed from the EB-rich extract (Extract2) prior to the PX recovery unit, eliminating the requirement of an additional fractionating tower.

TABLE 4

|  | OX | PX | MX | EB | PDEB |
|---|---|---|---|---|---|
| Feed (kg/min) | 164.9 | 306.4 | 645.3 | 181.8 | 0 |
| Desorbent (kg/min) | 0 | 0 | 0 | 0 | 1710.8 |
| Raffinate (kg/min) | 164.8 | 9.2 | 630.7 | 135.9 | 978.5 |
| Extract 1 (kg/min) | 0.03 | 264.2 | 0.1 | 0.81 | 672.6 |
| Extract 2 (kg/min) | 0.49 | 33.6 | 16.15 | 45.5 | 59 |

Table 5 shows the purity and recovery obtained in all of the product outlets. The PX-rich extract stream (Extract1) recovers 86.2 wt % of PX with 99.8 wt % purity. The EB-rich extract stream (Extract2) recovers an additional 11 wt % of PX to ensure an overall recovery of PX of more than 97 wt %, and recovers 25% of the total EB fed into the SMB system to further minimize EB build up in the xylene loop. The purity values of PX and EB in the EB-rich extract stream (Extract2) are 21.7 wt % and 29.4 wt %. This EB-rich extract stream (Extract2) can be either fed to a downstream SMB or a crystallizer to obtain pure PX and EB fractions.

TABLE 5

|  | OX | PX | MX | EB |
|---|---|---|---|---|
| Raffinate purity (wt %) | 17.5 | 0.98 | 67 | 14.5 |
| Raffinate recovery (wt %) | 99.9 | 3 | 97.7 | 74.8 |
| Extract 1 purity (wt %) | 0.01 | 99.7 | 0.04 | 0.3 |
| Extract 1 recovery (wt %) | 0.02 | 86.2 | 0.02 | 0.44 |
| Extract 2 purity (w/PDEB) (wt %) | 0.32 | 21.7 | 10.44 | 29.4 |
| Extract 2 recovery (w/PDEB) (wt %) | 0.3 | 11 | 2.5 | 25 |

Examples 1 and 2 illustrate the flexibility of the embodiments disclosed herein. Both examples describe a means of eliminating vapor phase isomerization, while creating a concentrated EB product stream. The mode of operation can be varied depending on the equipment limitations in the xylene loop. In Example 1, the recovery of pure PX product in Extract1 is higher, but at the cost of reduced EB recovery in the Extract2 stream, which will lead to larger recycle streams and a larger desorbent to feed ratio. Example 2 has a higher EB recovery in Extract2, which would reduce the size of recycle streams in the xylene loop, but at the cost of reduced recovery of PX in the Extract1 stream.

While various embodiments have been disclosed herein, modifications thereof can be made without departing from the scope or teachings herein. In particular, many variations and modifications of the systems, apparatus, and processes described herein are possible and are within the scope of the disclosed subject matter. Accordingly, embodiments disclosed herein are exemplary only and are not limiting. As a result, the scope of protection is not limited to the embodiments described herein, but is only limited by the claims that follow, the scope of which shall include all equivalents of the subject matter of the claims. Unless expressly stated otherwise, the steps in a method claim may be performed in any order. The use of identifiers such as (a), (b), (c) before steps in a method claim is not intended to and does not specify a particular order to the steps. Rather the use of such identifiers are used to simplify subsequent reference to such steps. Finally, the use of the term "including" in both the description and the claims is used in an open ended fashion, and should be interpreted as meaning "including, but not limited to".

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

The invention claimed is:

1. A process for recovering paraxylene, the process comprising:
    (a) introducing a first hydrocarbon feed stream into a first simulated moving bed adsorption unit, wherein the first hydrocarbon feed stream comprises a mixture of paraxylene (PX), metaxylene (MX), orthoxylene (OX), and ethylbenzene (EB);
    (b) introducing a desorbent stream into the first simulated moving bed adsorption unit, wherein the desorbent stream comprises a desorbent;
    (c) withdrawing a first PX-rich extract stream, which comprises desorbent and PX, from the first simulated moving bed adsorption unit, wherein the first PX-rich extract stream is withdrawn at a location downstream of a desorbent introduction location and upstream of a feed introduction location;
    (d) withdrawing an EB-rich extract stream, which comprises desorbent, EB, and PX, from the first simulated moving bed adsorption unit, wherein the EB-rich extract stream is withdrawn at a location downstream of the first PX-rich extract stream withdrawal location and upstream of the feed introduction location;
    (e) withdrawing a first PX-depleted raffinate stream, which comprises desorbent, MX, OX, and EB, from the first simulated moving bed adsorption unit;
    (f) isomerizing at least a portion of the first PX-depleted raffinate stream at least partially in a liquid phase to produce a first isomerized stream having a higher PX concentration than the first PX-depleted raffinate stream;
    (g) recycling at least a portion of the first isomerized stream to the first simulated moving bed adsorption unit; and
    (h) providing the EB-rich extract stream to a PX recovery unit to produce a second PX-rich extract stream, wherein the PX recovery unit comprises a second simulated moving bed adsorption unit or a crystallizer.

2. The process of claim 1, further comprising:
    (i) providing the first PX-rich extract stream to a first extract column to remove desorbent and produce a desorbent-free PX-rich extract stream; and
    (j) providing the desorbent-free PX-rich extract stream to a first finishing column to produce a first pure PX stream.

3. The process of claim 2, wherein the second PX-rich extract stream is provided to the first extract column of step (i).

4. The process of claim 3, wherein the second simulated moving bed adsorption unit produces a second PX-depleted raffinate stream, and further comprising recovering a pure EB stream from the second PX-depleted raffinate stream in a distillation column.

5. The process of claim 4, further comprising removing desorbent from the EB-rich extract stream before step (h).

6. The process of claim 4, wherein the second simulated moving bed adsorption unit comprises a different adsorbent than the first simulated moving bed adsorption unit, and wherein the adsorbent of the second moving bed adsorption unit has a higher affinity for EB and PX than the adsorbent of the first moving bed adsorption unit.

7. The process of claim 4, wherein a conventional simulated moving bed adsorption unit comprising 24 adsorbent beds, divided into two columns of 12 adsorbent beds each, is retrofitted such that the first column functions as the first simulated moving bed adsorption unit and the second column functions as the second simulated moving bed adsorption unit.

8. The process of claim 4, wherein the EB-rich extract stream is combined with a second hydrocarbon feed stream before step (h).

9. The process of claim 4, wherein the withdrawal location of the EB-rich extract stream from the first simulated moving bed adsorption unit is selected to minimize a desorbent content in the EB-rich extract stream, and the EB-rich extract stream comprises the entirety of a feed stream to the second simulated moving bed adsorption unit.

10. The process of claim 4, wherein the withdrawal location of the EB-rich extract stream from the first simulated moving bed adsorption unit is at least 3 beds away from the first PX-rich extract stream withdrawal location.

11. The process of claim 3, wherein the second simulated moving bed adsorption unit produces a second PX-depleted raffinate stream, and further comprising:
 (k) isomerizing at least a portion of the second PX-depleted raffinate stream in a vapor phase to produce a second isomerized stream having a higher PX concentration than the second PX-depleted raffinate stream; and
 (l) recycling at least a portion of the second isomerized stream to one or both of the first simulated moving bed adsorption unit and the second simulated moving bed adsorption unit.

12. The process of claim 3, wherein the second simulated moving bed adsorption unit produces an EB-rich raffinate stream and an EB-lean raffinate stream, and further comprising:
 (m) recycling at least a portion of the EB-lean raffinate stream to step (f); and
 (o) isomerizing at least a portion of the EB-rich raffinate stream in a vapor phase to produce a second isomerized stream having a higher PX concentration than the EB-rich raffinate stream.

13. The process of claim 2, wherein the PX recovery unit further comprises a crystallizer.

14. The process of claim 13, wherein the second PX-rich extract stream is provided to the first extract column of step (i).

15. The process of claim 14, wherein the crystallizer produces an EB-rich liquid product, which is sent to a refinery stream.

16. A process for recovering paraxylene, the process comprising:
 (a) providing a first hydrocarbon feed stream and a desorbent stream to a first simulated moving bed adsorption unit, wherein the first hydrocarbon feed stream comprises a mixture of paraxylene (PX), metaxylene (MX), orthoxylene (OX), and ethylbenzene (EB), and wherein the desorbent stream comprises desorbent;
 (b) withdrawing from the first simulated moving bed adsorption unit:
  (i) a first PX-rich extract stream, which comprises desorbent and PX;
  (ii) an EB-rich extract stream, which comprises desorbent, EB, and PX; and
  (iii) a first PX-depleted raffinate stream, which comprises desorbent, MX, OX, and EB,
 wherein the first PX-rich extract stream is withdrawn at a location downstream of a desorbent introduction location and upstream of a feed introduction location and the EB-rich extract stream is withdrawn at a location downstream of the first PX-rich extract stream withdrawal location and upstream of the feed introduction location;
 (c) isomerizing at least a portion of the first PX-depleted raffinate stream at least partially in a liquid phase to produce a first isomerized stream having a higher PX concentration than the first PX-depleted raffinate stream;
 (d) recycling at least a portion of the first isomerized stream to the first simulated moving bed adsorption unit;
 (e) providing the EB-rich extract stream to a second simulated moving bed adsorption unit to produce a second PX-rich extract stream and a second PX-depleted raffinate stream; and
 (f) recovering a pure EB stream from the second PX-depleted raffinate stream in a distillation column.

17. The process of claim 16, further comprising removing desorbent from the EB-rich extract stream before step (e).

18. The process of claim 16, wherein the EB-rich extract stream is combined with a second hydrocarbon feed stream before step (e).

19. The process of claim 16, further comprising removing $C_{9+}$ hydrocarbons from the first hydrocarbon feed stream in a xylenes fractionation column prior to step (a).

20. A process for recovering paraxylene, the process comprising:
 (a) providing a first hydrocarbon feed stream and a desorbent stream to a first simulated moving bed adsorption unit, wherein the first hydrocarbon feed stream comprises a mixture of paraxylene (PX), metaxylene (MX), orthoxylene (OX), and ethylbenzene (EB), and wherein the desorbent stream comprises desorbent;
 (b) withdrawing from the first simulated moving bed adsorption unit:
  (i) a first PX-rich extract stream, which comprises desorbent and PX;
  (ii) an EB-rich extract stream, which comprises desorbent, EB, and PX; and
  (iii) a first PX-depleted raffinate stream, which comprises desorbent, MX, OX, and EB,
 wherein the first PX-rich extract stream is withdrawn at a location downstream of a desorbent introduction location and upstream of a feed introduction location and the EB-rich extract stream is withdrawn at a location downstream of the first PX-rich extract stream withdrawal location and upstream of the feed introduction location;
 (c) isomerizing at least a portion of the first PX-depleted raffinate stream at least partially in a liquid phase to produce a first isomerized stream having a higher PX concentration than the first PX-depleted raffinate stream;
 (d) recycling at least a portion of the first isomerized stream to the first simulated moving bed adsorption unit;
 (e) providing the EB-rich extract stream to a second simulated moving bed adsorption unit to produce a second PX-rich extract stream and a second PX-depleted raffinate stream;
 (f) isomerizing at least a portion of the second PX-depleted raffinate stream in a vapor phase to produce a second isomerized stream having a higher PX concentration than the second PX-depleted raffinate stream; and
 (g) recycling at least a portion of the second isomerized stream to the first simulated moving bed adsorption unit or the second simulated moving bed adsorption unit.

21. The process of claim 20, further comprising removing $C_{7-}$ hydrocarbons from the second isomerized stream in a fractionation column prior to step (g).

22. The process of claim 20, further comprising removing $C_{9+}$ hydrocarbons from the second isomerized stream in a xylenes fractionation column prior to step (g).

* * * * *